(12) United States Patent
Cooper et al.

(10) Patent No.: US 10,093,591 B2
(45) Date of Patent: Oct. 9, 2018

(54) METHOD OF CHARACTERISING THE STRUCTURE OF A VOID SENSITIZED EXPLOSIVE COMPOSITION

(71) Applicant: Orica International Pte Ltd, Singapore (SG)

(72) Inventors: John Cooper, Ayr (GB); Ian John Kirby, Ayr (GB); Vladimir Sujansky, East Burwood (AU); Sek K Chan, Pierrefonds (CA)

(73) Assignee: Orica International Pte Ltd, Singapore (SG)

( * ) Notice: Subject to any disclaimer, the term of this patent is extended or adjusted under 35 U.S.C. 154(b) by 227 days.

(21) Appl. No.: 14/365,978

(22) PCT Filed: Dec. 13, 2012

(86) PCT No.: PCT/AU2012/001528
§ 371 (c)(1),
(2) Date: Jun. 16, 2014

(87) PCT Pub. No.: WO2013/086573
PCT Pub. Date: Jun. 20, 2013

(65) Prior Publication Data
US 2015/0218061 A1  Aug. 6, 2015

(30) Foreign Application Priority Data
Dec. 16, 2011 (AU) .................. 2011905263

(51) Int. Cl.
*C06B 31/00* (2006.01)
*C06B 45/00* (2006.01)
(Continued)

(52) U.S. Cl.
CPC ............ *C06B 31/00* (2013.01); *C06B 23/003* (2013.01); *C06B 23/004* (2013.01); *C06B 45/00* (2013.01); *G01N 33/227* (2013.01); *G01N 33/22* (2013.01)

(58) Field of Classification Search
CPC ........ C06B 31/00; C06B 45/00; C06B 23/003
See application file for complete search history.

(56) References Cited

U.S. PATENT DOCUMENTS 3,774,496 A    11/1973    Roach
3,797,392 A    3/1974    Eckels
(Continued)

FOREIGN PATENT DOCUMENTS

CN    103193557 A    7/2013
EP    0136081 B1    11/1987
(Continued)

OTHER PUBLICATIONS

Patent Examination Report No. 1 for Australian Application No. 2012350356, dated Jun. 11, 2015, 3 pages.
(Continued)

*Primary Examiner* — Aileen B Felton

(57) ABSTRACT

A method of characterizing the structure of a void sensitized liquid energetic material, which method comprises defining the material in terms distribution function, the distribution function representing the fraction of liquid energetic material that occurs at a given point within the void sensitized liquid energetic material.

10 Claims, 13 Drawing Sheets

(51) Int. Cl.
*C06B 23/00* (2006.01)
*G01N 33/22* (2006.01)

(56) References Cited

U.S. PATENT DOCUMENTS

| | | |
|---|---|---|
| 4,104,092 A | 8/1978 | Mullay |
| 4,326,900 A | 4/1982 | Hattori et al. |
| 4,554,032 A | 11/1985 | Hattori et al. |
| 4,614,146 A | 9/1986 | Ross et al. |
| 4,757,764 A | 7/1988 | Thureson et al. |
| 5,099,763 A * | 3/1992 | Coursen ............... C06B 45/00 102/313 |
| 5,346,564 A * | 9/1994 | Vance .................. C06B 21/00 149/109.6 |
| 5,470,407 A | 11/1995 | Griffith et al. |
| 5,524,523 A | 6/1996 | Lübbe et al. |
| 5,584,222 A | 12/1996 | Engsbråten et al. |
| 5,712,440 A | 1/1998 | Eagar et al. |
| 5,783,768 A | 7/1998 | Jacobson |
| 6,125,761 A | 10/2000 | Smith, Jr. et al. |
| 6,165,297 A | 12/2000 | Smith et al. |
| 6,173,662 B1 | 1/2001 | Donovan |
| 6,397,719 B1 | 6/2002 | Vestre |
| 6,537,399 B2 | 3/2003 | Gomez De Segura et al. |
| 6,669,753 B1 | 12/2003 | Chambers et al. |
| 6,877,432 B2 | 4/2005 | Thomson et al. |
| 6,982,015 B2 | 1/2006 | Atkinson et al. |
| 7,370,565 B2 | 5/2008 | Pressley et al. |
| 7,971,534 B2 | 7/2011 | Waldock |
| 8,230,937 B1 | 7/2012 | Asay et al. |
| 8,708,202 B2 | 4/2014 | Robertson et al. |
| 8,820,242 B2 | 9/2014 | Alexander |
| 9,175,933 B2 | 11/2015 | Patel |
| 9,207,055 B2 | 12/2015 | Halander et al. |
| 9,267,777 B2 | 2/2016 | Waldock |
| 9,415,360 B2 | 8/2016 | Xue |
| 9,435,625 B2 | 9/2016 | Halander et al. |
| 2003/0006319 A1 | 1/2003 | Silverstein et al. |
| 2003/0029346 A1 | 2/2003 | Atkinson et al. |
| 2014/0352567 A1 | 12/2014 | Cooper et al. |
| 2016/0145165 A1 | 5/2016 | Zank et al. |
| 2016/0146587 A1 | 5/2016 | Zank et al. |

FOREIGN PATENT DOCUMENTS

| | | |
|---|---|---|
| EP | 0142271 B1 | 2/1988 |
| EP | 1571136 A2 | 9/2005 |
| GB | 2218701 A | 11/1989 |
| GB | 2338429 A | 12/1999 |
| NL | 6918158 A | 6/1971 |
| WO | WO 1997/024298 A1 | 7/1997 |
| WO | WO 1997/030955 A1 | 8/1997 |
| WO | WO 2002/024608 A1 | 3/2002 |
| WO | WO 2009/092137 A1 | 7/2009 |
| WO | WO 2013/086572 A1 | 6/2013 |

OTHER PUBLICATIONS

Office Action for European Application No. 12857454.8, dated Feb. 27, 2017, 9 pages.
Supplementary European Search Report for European Application No. 12857454.8, dated May 8, 2015, 8 pages.
Maron, S. H. et al., "Fundamentals of Physical Chemistry," Editorial Limusa S.A. Mexico, 1978, p. 469, 3 pages.
International Search Report and Written Opinion for International Application No. PCT/AU2012/001528, dated Feb. 7, 2013, 12 pages.
3M Microspheres, Technical Data Sheet, K Series, S Series Energy and advanced materials division, 2007.
Wang, X., "Explosive emulsion," Metallurgical Industry Press, 1994, p. 6, 4 pages.

* cited by examiner

METHOD OF CHARACTERISING THE STRUCTURE OF A VOID SENSITIZED EXPLOSIVE COMPOSITION

CROSS REFERENCE TO RELATED APPLICATIONS

This application is a national stage filing under 35 U.S.C. § 371 of International Patent Application No. PCT/AU2012/001528, filed Dec. 13, 2012 and entitled "A Method of Characterising the Structure of a Void Sensitized Explosive Composition," which claims priority to Australian Patent Application No. 2011905263, filed Dec. 16, 2011.

TECHNICAL FIELD

The present invention relates to a method of characterizing the internal structure of certain types of explosive compositions and to understanding how the internal structure relates to bulk detonation properties in terms of energy release profile of the explosive compositions. The present invention also relates to the design of new explosives compositions based on the relationship between internal structure and bulk detonation properties.

BACKGROUND OF THE INVENTION

There are various types of explosive composition that are used in commercial mining and blasting operations. The context of use will dictate the explosive composition that is employed based on such factors as the energy release characteristics of the explosive composition and current commercial explosives offer a range of shock and heave energies. For example, ANFO (ammonium nitrate/fuel oil) tends to provide low shock energy and high heave energy and this tends to be thought of as an excellent combination for many rock blasting and collection applications. In contrast, emulsion based explosives tend to provide high shock energy and low heave energy. It would be desirable to control the energy release characteristics of emulsion-based explosives in terms of shock and heave energies thereby increasing the range of practical use of such explosives. It would be particularly desirable to provide emulsion-based explosives that behave more like ANFO with respect to detonation performance.

There is also a need to have a greater understanding of the structural features of explosive formulations and how these structural features influence detonation characteristics. In turn, it is believed that this understanding will facilitate the design of explosive formulations that have novel (internal) structures, novel detonation characteristics and energy release profiles that can be manipulated and tailored to a particular context of use.

SUMMARY OF THE INVENTION

The present invention focuses on void-sensitized liquid energetic materials, such as emulsion explosives. This type of explosive formulation is well known and commonly used in the art. Emulsion explosives include voids distributed in a liquid energetic material, the voids rendering the explosive detonable. The voids may be in the form of gas bubbles, glass microballoons, plastic microballoons, expanded polystyrene spheres, and indeed any cavities that produce a low density region in the liquid explosive. For commercial mining explosives the average mean diameter of the voids can range from 25 microns to 500 microns. The lower end of void size is limited by the need for the void to act as an ignition point in the explosive and the upper end is limited by the need for the explosive to fully react. Preferably, an optimum voidage is incorporated in order to achieve satisfactory detonation propagation in terms of a critical diameter of the explosive charge and critical velocity of detonation. By using the minimum amount of voids it is possible to retain relatively high density of the resultant composition.

Typically, the total volume (voidage) occupied by the voids in the composition is at least 3% based on the total volume of the composition. Usually, the total volume of the voids is at least 10% by volume, for instance up to about 20% by volume. Inclusion of an amount of voids (or cavities) over and above the critical amount required for sensitization will unnecessarily reduce the density of the composition and lead to reduced energy-density of the resultant explosive material.

In the context of the present invention sensitizing voids may be gas bubbles, glass microballoons, plastic microballoons, expanded polystyrene beads, or any other material with a density below 0.25, with the voids having a mean diameter in the range 20 to 2000, preferably in the range 40 to 500 microns.

In accordance with the present invention it has been found that this type of explosive composition possesses structural features that can readily be tailored to influence detonation characteristics. The present invention provides a new way of defining the structure of an explosive material that comprises sensitizing voids distributed in a continuum of liquid energetic material. Specifically, in accordance with the present invention it has been found that the structure can be represented by a statistical/mathematical model. Moreover, it has been found that this model can be related to the bulk detonation properties of the explosive materials in terms of detonation and burning reactions. These reactions are related to the energy release profile associated with explosive materials in terms of the partitioning between shock and heave energies. Shock energy is related to detonation reactions and heave energy is related to (the efficiency of) burning reactions. This approach can be applied to characterize the structure and to understand the detonation behavior of known void sensitized liquid energetic materials. It may also be applied to characterize the structure and to understand/predict the detonation behavior of newly designed and formulated void sensitized liquid energetic materials.

In accordance with an embodiment of the invention it is possible to relate desirable bulk detonation properties of this type of explosives material to a statistical/mathematical model that represents the distribution of sensitizing voids within a (continuum of) liquid energetic material, and from that model to derive structural templates (in terms of void distribution) that will yield those detonation properties. This embodiment may therefore be regarded as a design tool for the formulation of void-sensitized liquid energetic materials.

The present invention uses what is referred to herein as a "distribution function" (DF) to characterize an explosives material in terms of its internal structure with respect to the distribution of sensitizing voids within a (continuum of) liquid energetic material. The "distribution function" (DF) is the fraction of liquid energetic material that is within a given distance from any void surface. Accordingly, in one embodiment the present invention provides a method of characterising the structure of a void sensitized liquid energetic material, which comprises determining for the material (defining the material in terms of) the fraction of liquid energetic material that occurs at a given distance from any void surface within the void sensitized liquid energetic material. This determination results in a distribution function template for the void-sensitized liquid energetic material.

The distribution functions are believed to be new per se and the invention also relates to them as such.

Those skilled in the art of statistical mechanics may see similarities between the distribution function as used in the present invention and the concept of radial distribution function (DF) or pair correlation function that has been applied to describe how the atomic density in a material varies as a function of the distance from a particular atom. One of the uses of the radial distribution function is in providing mathematical relationships that define thermodynamic properties of a material in terms of the positions of atoms in that material.

As will be explained, the bulk detonation energy output for a void-sensitized liquid energetic material can be related to the DF template of the material. Accordingly, in another embodiment the present invention provides a method of achieving a designed bulk detonation energy output in an explosives material comprising sensitizing voids distributed within a liquid energetic material, which method comprises determining a distribution function template that is representative of the designed detonation energy output for the explosives material and formulating an explosive material consistent with that distribution function template by suitable placement and distribution of sensitizing voids within a liquid energetic material. In an embodiment of the invention this may be done by suitable combination of a void-sensitized liquid energetic material with a void-free liquid energetic material. In accordance with the present invention it has been found that structure and detonation properties of the resultant composition is related to the volume ratio of each energetic liquid and the structural arrangement of the energetic liquids relative to each other.

In this embodiment the internal structure of the explosive composition is such that the two energetic materials are present as discrete regions. These regions may be distributed uniformly or randomly throughout the composition. The volume proportion, size and spatial arrangement of the regions define the bulk explosive structure. It has been found that the nature of the energetic liquids used and the bulk structure of the resultant explosive composition influences the energy release characteristics of the explosive composition. Thus, the voids, after their reaction determine amount of shock energy and the regions of void-free liquid energetic material determine the heave energy. Quantitatively, the amount of shock energy is a function of the "total voidage volume" and the amount of heave energy is a function of the void-free component volume fraction.

Importantly, this embodiment allows the energy release characteristics of an explosive composition to be understood and controlled by varying the combination of energetic liquids used and/or the arrangement of the energetic liquids within the bulk of the explosive composition. In turn this enables the detonation properties of the explosive composition to be tailored to particular rock/ground types and to particular mining applications.

While this invention is concerned with the design of liquid explosives, and the detonation performance is determined by the distribution of the voids in the liquid, this does not preclude the addition of small quantities of energetic solids such as aluminium and/or ammonium nitrate prills to further modify the detonation performance.

The present invention also relates to the design of new liquid explosive compositions with novel geometrical distributions of sensitizing voids. A method of mathematically characterizing the internal structure of these explosive compositions is presented. Also an empirical relationship between the internal structure and the bulk detonation properties has been found. A particular advantage of these liquid explosives is the higher energy densities and much higher heave energies that are achievable compared with conventional liquid explosives.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

BRIEF DISCUSSION OF DRAWINGS

DETAILED DISCUSSION OF THE INVENTION

Figure 1:
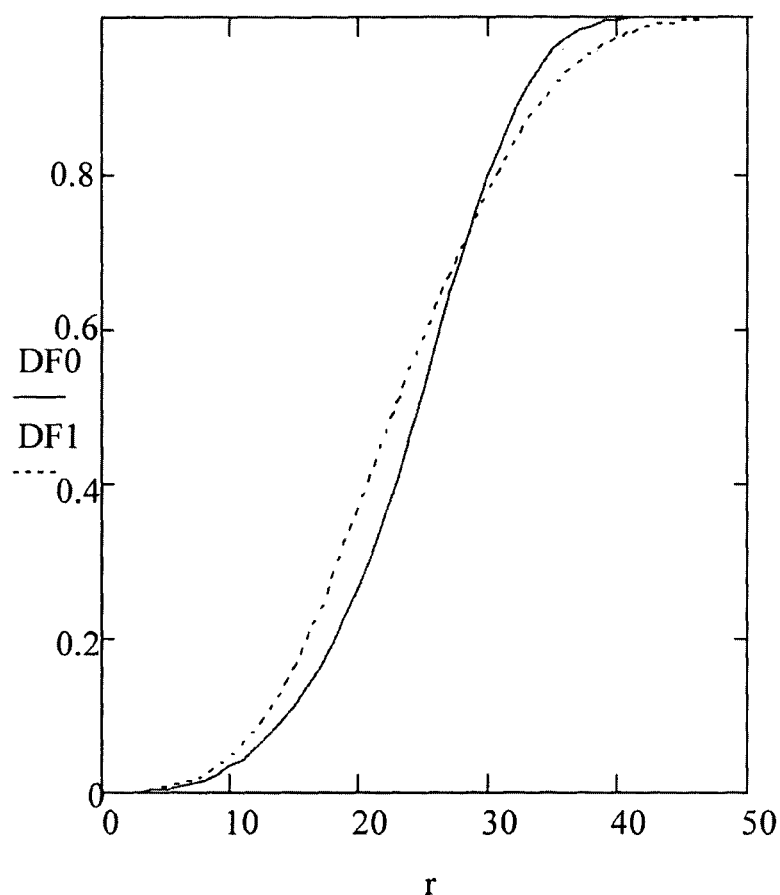
FIG. 1 shows Distribution Function templates for conventional void-sensitized explosive formulations.

As noted above, in the context of the present specification, the distribution function (DF) for a void-sensitized liquid energetic material is a statistical representation of the fraction of liquid energetic material that is within a given distance from any void surface. This can be illustrated with reference to FIG. 1 below. FIG. 1 shows DF templates that are representative of conventional emulsion explosives in which a liquid energetic material is sensitized by the inclusion of voids. The voids have a random distribution in the liquid energetic material.

In FIG. 1 the y-axis is the fraction of liquid energetic material within a distance "r" from any void surface and the x-axis represents the radial distance from the nearest void surface. The solid line, DF0 template, represents a theoretical emulsion in which the voids, are at the centers of an array of 50 micron cubes, and "r" is the distance from the nearest void surface. The dotted line, DF1 template, represents a conventional emulsion of the same density as the cubic array, but with a random distribution of the voids, 95% having separations between 35 to 60 microns (a random generator picks positions in a 50 micron cubic grid so that voids can be placed randomly in the grid until the target voidage (density) is reached). This random distribution of voids is consistent with what one would observe in conventional emulsion explosives that are formulated by distributing sensitizing voids within a liquid energetic material.

In practice, the randomness of the distribution of the voids will depend on the mixing procedure used, and the corresponding DF may vary from the DF1 template slightly. Nevertheless, it is believed that such changes would not be dramatic: the curve would still be sigmoid in nature and there would be no abrupt changes in the slope of the curve. In relation to such conventional void-sensitized liquid energetic materials the present invention resides in the application of DF to describe/represent the internal structure of the material. The application of statistical modeling involving DF to explosives is unique in this regard.

The present invention is also concerned however with characterizing the internal structure of explosives materials that are new with respect to how voids are distributed within a liquid energetic material, and to the corresponding DF templates associated with such new explosives materials. Noting the random manner in which voids are present in conventional void-sensitized explosive materials, in general terms this new internal structure may be described as involving a non-random (or designed) distribution of voids. In view of this fundamental difference in void distribution, these new explosive materials will have different DF templates when compared with the DF templates associated with conventional materials.

Figure 2:
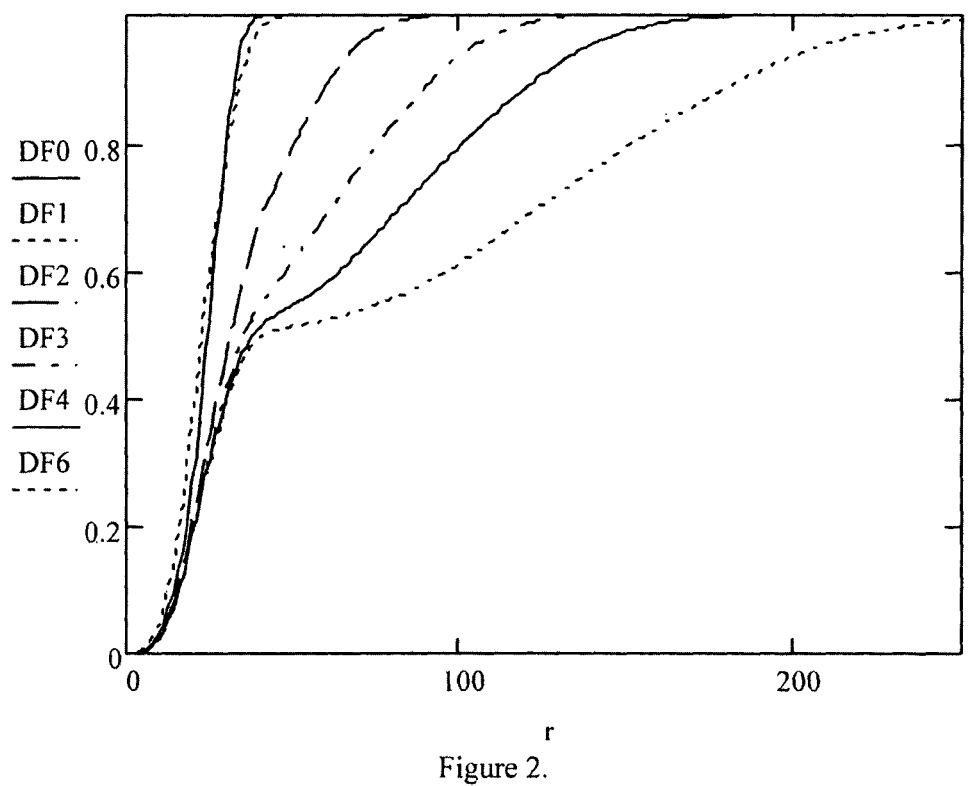
FIG. 2 shows Distribution Functions templates for conventional and non-conventional void-sensitized explosive formulations.

This embodiment of the present invention may be illustrated with reference to unique forms of explosive formulation that have a non-random distribution of voids in a liquid energetic material. Specifically, this explosive is manufactured by blending a void-free energetic liquid with conventional void sensitized energetic liquid. These formulations are referred to as mixtures of emulsion, designated MoE. Careful blending is undertaken to ensure that the finished formulation includes discrete regions of the individual component liquid energetic materials. The explosive can be conveniently prepared by laminar mixing of streams of the individual components using a static mixer (see for example FIG. 7 and the accompanying discussion). By this mixing methodology the streams of the individual components are split into sheets that have a mean thickness typically in the range 0.2 to 50 mm. It is to be understood however that sheets of larger thicknesses could be employed without deviating from the spirit of the invention. The characteristics of the sheets can be adjusted by adjusting the mixing methodology, for example by varying the number of mixing elements in the static mixer. DF templates for a number of formulations with varying dimensions of the void-free regions of liquid energetic material were modeled using the DF procedure described above. FIG. 2 is a plot as per FIG. 1 showing how the DF varies for each formulation.

In relation to FIG. 2:
Template (DF0) and Template (DF1) are the same as in FIG. 1, and correspond to the theoretical and conventional void-sensitized emulsions.
Template (DF2) relates to a 50:50 blend of the conventional void sensitized emulsion and void-free emulsion in which the regions of void-free emulsion have dimensions ranging from 2 to 4 times the diameter of the voids in the sensitized emulsion.
Template (DF3) relates to a 50:50 blend of the conventional void sensitized emulsion and an void-free emulsion in which the regions of void-free emulsion have dimensions ranging from 3 to 6 times the diameter of the voids in the sensitized emulsion.
Template (DF4) relates to another equal blend of the conventional void-sensitized emulsion and an void-free emulsion, but in this case the regions of void-free emulsion have dimensions ranging from 4 to 8 times the diameter of the voids in the sensitized emulsion.
Template (DF6) exhibits simply a coarser blend of sensitized and void-free emulsions in which the regions of void-free emulsion have dimensions ranging from 6 to 10 times the diameter of the voids in the sensitized emulsion.

It will be noted that the formulations in which the voids are provided with a non-random (designed) distribution give rise to DFs that have increasingly different shapes from those for conventional emulsions, i.e. DF0 and DF1. For formulations having a non-random void distribution, the plot of DF against radial distance (r) departs from that of conventional formulations with this departure becoming more exaggerated as the dimensions of the void-free emulsion increases.

For DF2, DF3, DF4 and DF6 the exact shape of the curve will vary depending on such factors as the voidage level of the sensitized emulsion and the void distribution of that emulsion.

An alternative method of displaying the differences between DFs for the conventional and non-random void sensitized formulations is to plot the differential of the DF with respect to the distance from the nearest void surface "r", against the "DF". This produces a graph that is similar in form to the conventional way of displaying reaction kinetics in the modelling of detonation. In this the reaction rate is plotted against the fraction of material reacted.

Figure 3:
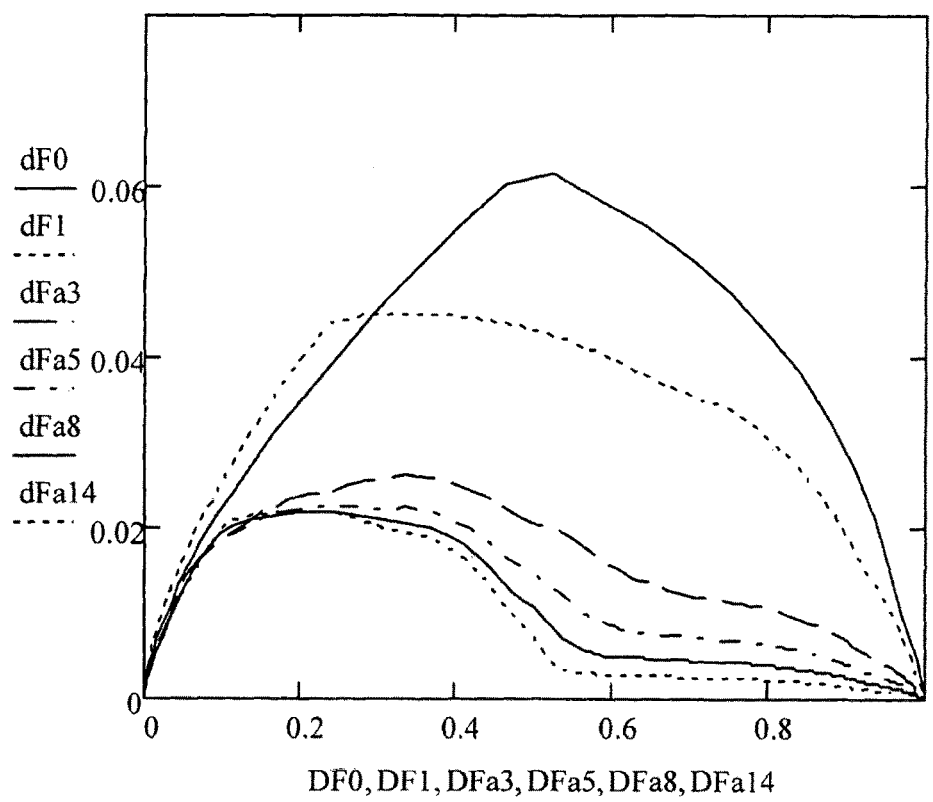
FIG. 3 shows the differential of Distribution Functions for conventional and non-conventional void-sensitized explosive formulations.

Such a DF rate plot is shown in FIG. 3 where the y-axis is the rate of change of the distribution function from the nearest void surface ("r") (DF rate) and the x-axis is the unity normalized distribution function.

In relation to FIG. 3:
Template (DF0) and Template (DF1) correspond to the theoretical and conventional emulsion blends as shown in FIG. 1.
DFa3, DFa5, DFa8 and DFa114 are 50:50 blends of a conventional emulsion and an unsensitized emulsion in which the conventional emulsion is distributed as droplets/globules in a continuum of the unsensitized emulsion, the diameters of the droplets/globules being approximately 3, 5, 8 and 14 times the average diameter of the voids.

Various aspects are worthy of comment:

The first point to notice with this method of displaying information is the "dome" shape of the distribution function curves.

For the conventional emulsions the "dome" is more or less symmetrical, remaining convex over "DF" values (x-axis) from 0 to 1. However, this is not the case for the non-conventional formulations, where the domed portion of the curve extends approximately only from "DF" values (x-axis) 0 to 0.5, after which the curve has a point of inflexion and transitions to a concave shape. It will be shown later that emulsions that exhibit this characteristic point of inflexion and concave shape in their DF curve exhibit reduced VODs relative to conventional emulsions with symmetrical, convex DF curves.

For the non-conventional formulations the maximum value of DF rate over the DF range from 0 to 1 is significantly less than for the conventional formulations.

The non-conventional formulations exhibit increasingly lower values of "DF rate" (y-axis) and reduced slope gradient at values of "DF" above 0.5. This is the consequence of distance between (r) the sensitizing voids becoming greater.

The emulsions prepared by conventional methods exhibit comparable "DF rate" of non-conventional materials only at DF values between 0.85 and 1.0.

The DF rate templates for the non-conventional formulations correspond to emulsion blend ratios of sensitized to dense emulsions from 10% to 90%, which roughly correspond to the transition from the "dome" region to the lower "DF rate" region occurring at "DF" values between 10% and 85%.

Figure 4:
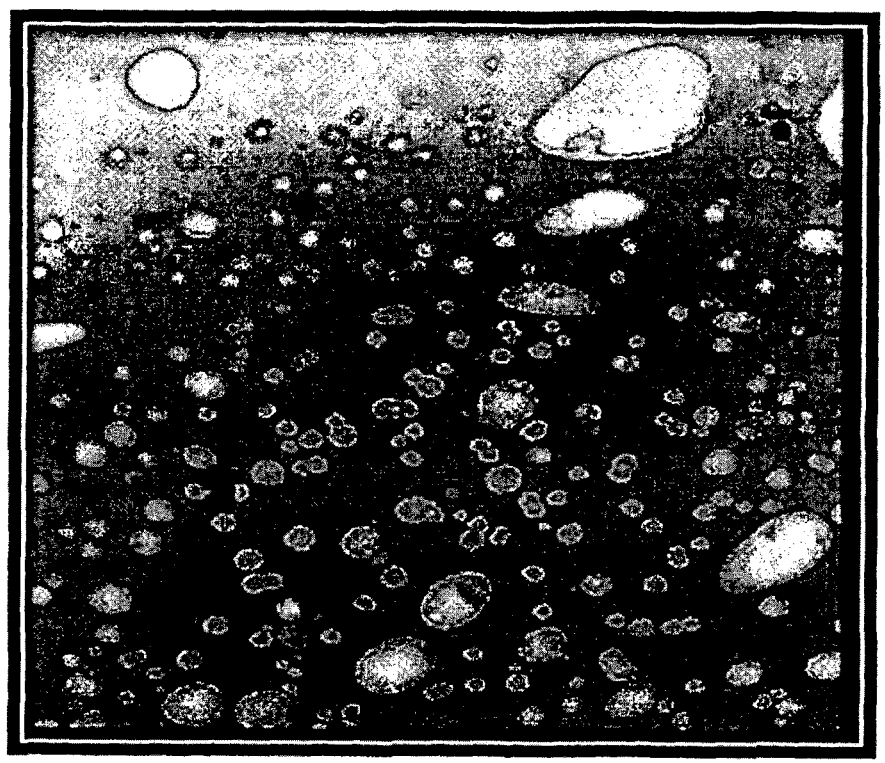
FIG. 4 is an X-ray image of a conventional void-sensitized explosive formulation.

Experimental measurements of the distribution functions (DFs) of conventional emulsions (random distribution of voids) were carried out using an X-ray tomography method to record the positions and sizes of voids in a 10 mm×10 mm×1 mm sample of a gassed emulsion. The two dimensional digital record of this was analyzed using commercial image analysis software that identified the outer edges of all the voids, and provided a digital output of the coordinates of the centre and length of the circumference of each void. This data was then used to generate templates for the "DF rate" plots. An X-ray tomography image and analysis of a conventional gas-void emulsion is shown in FIG. 4. The circumference of lighter of the voids is analysed, noting also that certain features were identified as ammonium nitrate crystals where the emulsion has broken down.

Figure 5:
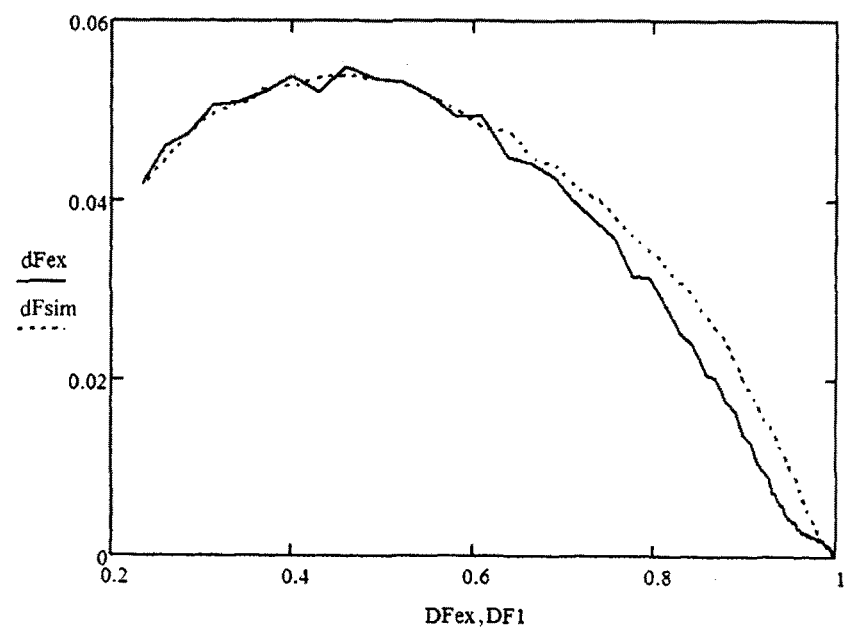
FIG. 5 shows the differential of Distribution Functions for conventional and non-conventional void-sensitized explosive formulations.

The data from this two dimensional analysis was also used to generate "DF rate" graphs. This was done by calculating the distance of each pixel of the digital image that corresponds to emulsion, from the nearest void surface, a computationally intensive operation. The resultant graph of the experimental DF is shown in FIG. 5. FIG. 5 is a representation of distribution function rate (DF rate) for the experimental X-ray image analysis of the experimental data.

DFex is the experimental data for a conventional emulsion in which voids cover about 20% of the area, the traces therefore stopping below this value on the x-axis.

DFsim is a simulated conventional emulsion in which the void size distribution and average void concentration is set approximately equal to that of the experimental data.

It will be noted that DFex and DFsim in FIG. 5 exhibit a convex shape consistent with the convex shape of plots for DF0 and DF1 in FIG. 3.

From the foregoing it should be apparent how to generate DF profile templates for void sensitized formulations. The approach may be especially useful for generating DF templates for non-conventional formulations that are typically prepared by blending a conventional void sensisitized emulsion with a void-free (or differently sensitized) continuum of liquid energetic material.

Figure 6:
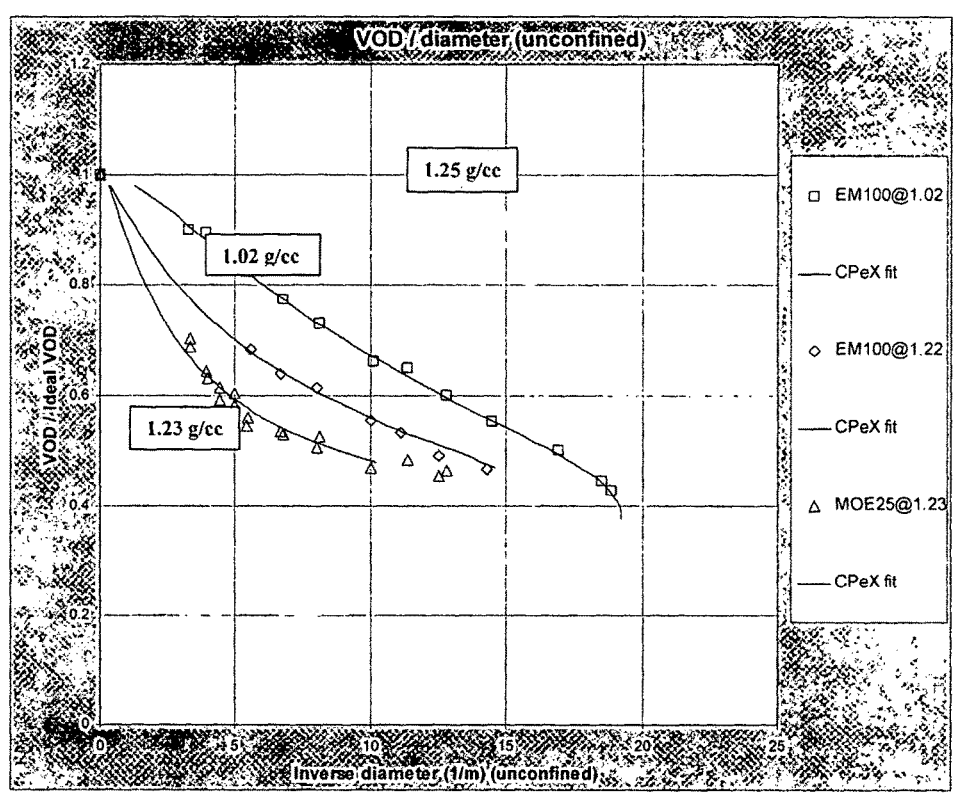
FIG. 6 is a plot comparing VOD against inverse/diameter for two conventional void-sensitized explosive formulations and for one non-conventional void-sensitized explosive formulation.

FIG. 6 shows a plot of velocity of detonation (VOD) divided by ideal VOD versus inverse diameter, where the ideal VOD is calculated by application of hydrodynamic theory, for example the Orica Ltd program IDEX. The figure plots results for two conventional explosive formulations and one non-conventional explosive formulation for charge diameters in range between 40-300 mm.

The conventional charges were samples of AN-based emulsion explosives prepared by a conventional methodology at densities equal to 1.22 and 1.02 g/cm$^3$ for EM 100 both exhibiting a random distribution of sensitizing voids. The total sensitizing voids volume was equal to about 5.3% for EM 100 at 1.22 g/cm$^3$ and 23% for EM 100 of the AN-based liquid energetic material continuum. The latter was the same for both formulations. With regard to VOD data the solid lines in FIG. 6 are fits to a theoretical model of non-ideal detonation.

The main point to note from, this experiment is that the emulsion prepared by a conventional method as per DFsim/DFex templates exhibits an approximately straight line relationship of VOD/idealVOD against inverse diameter. The DF rate profiles for these conventional formulations are reasonably matched to be in line with the DFsim/DFex template in FIG. 5 above.

A non-conventional emulsion explosive formulation (denoted MOE25) was prepared according to a selected DF rate design template produced in accordance with the present invention. The non-conventional formulation was a blend of 25% mass void sensitized liquid energetic material (density 1.02 g/cc) and 75% mass void-free liquid energetic material continuum (density 1.32 g/cc). The liquid energetic material used was the same as used in formulating the conventional EM 100 control samples. The resulting explosive charges of MOE25 had a density of 1.23 g/cc.

Figure 7:
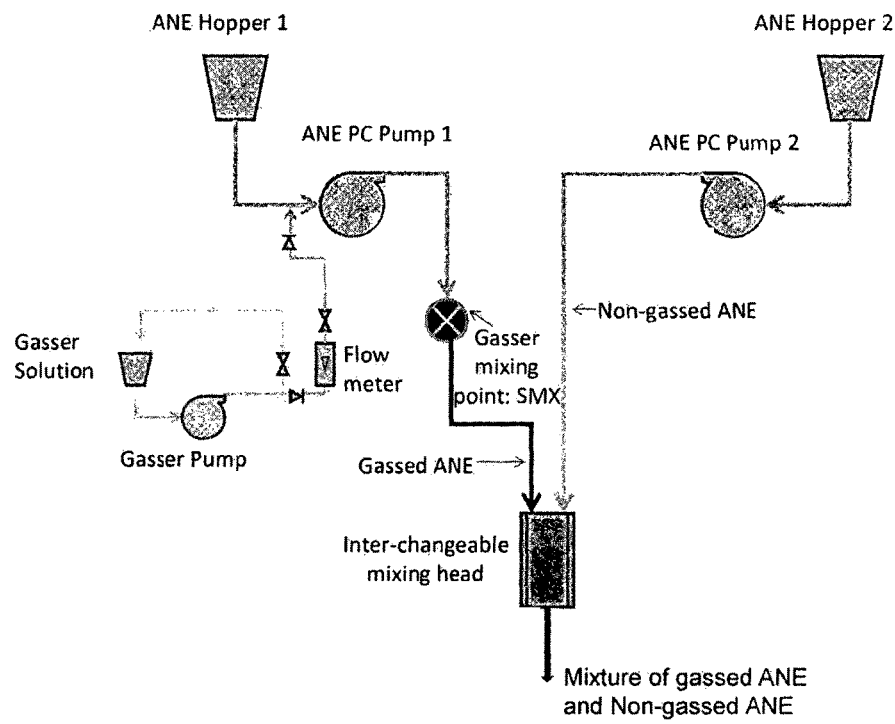
FIG. 7 is a schematic illustrating an apparatus referred to in the examples.

Experimental samples were prepared in a specially designed emulsion experimental rig shown in FIG. 7 and described in Example 1.

Notably, the relationship between VOD against inverse diameter for this non-conventional formulation was very different from that of the conventional control sample. Indeed, considering that the liquid energetic material continuum used is identical, it is remarkable to see the vast difference between the VOD characteristics for these formulations.

More importantly, the non-conventional formulation shows a characteristic highly concave variation of unconfined normalised detonation velocity (VOD/idealVOD) versus inverse diameter. In contrast, the formulations prepared by conventional methodology exhibit an approximately straight or slightly concave shape from the critical diameter to the ideal VOD.

It is well known to those skilled in the art that at a given explosive density, the shock energy increases with increasing VOD, and that a reduction in VOD corresponds to an increase in heave energy.

For a given liquid energetic material, it is important to note that lower VODs can be obtained in conventional formulations by reducing density, i.e. by increasing the level of voidage include in the liquid energetic material. However, an undesirable effect of this is reduced energy density output and thus lower heave and shock energy.

In distinct contrast, the formulation provided in the present invention enables reduced VOD to be achieved without reducing overall energy density. Thus, such non-conventional formulations may provide a remarkable enhancement in energy density as well as enhanced and unique partitioning of heave energy to shock energy.

In practice implementation of the design aspect of the present invention is likely to involve the following sequence of steps, given by way of illustration with reference to a particular example:
1. Select the density of the void-free liquid energetic material being used and the desired density of the high energy density/high heave charge to be formulated. For example, the density of the void-free liquid energetic material may be 1.32 g/cc and the required density of the explosive charge to be produced is 1.23 g/cc.
2. Calculate the total volume of the voidage that needs to be incorporated to achieve the required density. Calculated voidage volume is (100)−(1.23/1.32×100)=6.8%. Note: this is not necessary for gas sensitized emulsions. However, it is helpful in case of micro-balloons as sensitizing agent or other material voids when the particle density is known. The required mass of balloons to achieve voidage-density can be then calculated.
3. Select the mean size of the voids to be used for sensitization. For example, the mean size of the voids might be 150 μm (Measure the size distribution if desired).
4. Select the DF template to obtain desirable VOD (shock/heave ratio), for example, the DF4 template. This template represents 50/50 volume fine blend of conventional void sensitized liquid energetic material and void-free liquid energetic material.
5. Calculate the required density of sensitized energetic material that gives the final density of 1.23 g/cc when mixed 50/50 with void-free liquid energetic material, i.e. 1.14 g/cc.
6. Blend 50% sensitized conventional liquid energetic material (density of 1.14 g/cc) and 50% void-free liquid energetic material (density of 1.32 g/cc) utilizing process consistent with achieving the DF4 template.
7. The DF4 template requires the high density regions to have dimensions equal to 4-8 times the diameter of the voids. Calculate the size of the dense emulsion regions as (150 μm×4)=600 μm and (150 μm×8)=1200 μm.
8. Select the "static mixer blending head" with laminar flow design such that individual streams of sensitized and void-free components are provided within the thickness specified by DF4 template. This is 600-1200 μm.

Embodiments of the present invention are illustrated with reference to the following non-limiting examples.

EXAMPLES

Description of Equipment

Experimental samples were prepared in a specially designed emulsion experimental rig. The corresponding process diagram is shown in FIG. 7. With reference to that figure the experimental rig comprises two emulsion holding hoppers ANE1 and ANE2. Two metering pumps PC Pump 1 and PC Pump 2 supply streams of the emulsions into an inter-changeable mixing head. The mass flow of the individual fluid streams is set up by calibration of the metering pumps and cross-checking against the total mass flow via into the inter-changeable mixing head. Blending is done in a continuous manner in the closed pipe of a interchangeable mixing head module.

The inter-changeable mixing head is comprised of two parts. The first part has two separate inlet channels for the entry of each emulsion stream and a baffle just before the entrance to the first static mixer element to ensure separation of the individual streams in the mixing section. The inter-changeable mixing head is 50 mm diameter and length of 228 mm.

Figure 8:
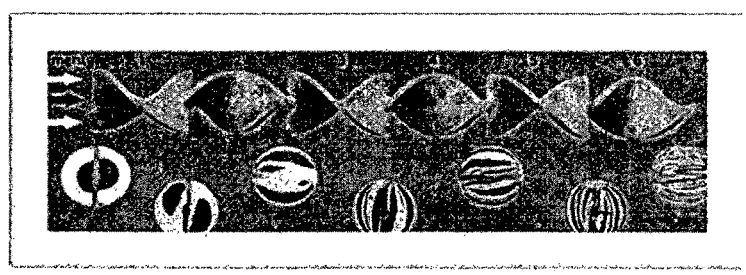
FIG. 8 is a schematic illustrating a mixing element referred to in the examples.

A Kenics static mixer (having 3 elements; see FIG. 8) was used for layering the void sensitized emulsion into the void-free high density emulsion continuum through laminar flow of two continuous streams of the emulsions. Laminar mixing is achieved by repeated division, transposition and recombination of liquid layers around a static mixer. In this way, the components of emulsion to be mixed are spread into a large number of layers. A clearly defined and uniform shear field is generated through mixing. Addition of further static mixer elements (for example No 4, 5 & 6) reduces the thickness of the layers produced.

The density change of the gassing emulsion was determined in a plastic cup of known mass and volume. The emulsion was initially filled to the top of the cup and leveled off. As the gassing reaction progressed, the emulsion rose out of the top of the cup and was leveled off periodically and weighed. The density was determined by dividing the mass of emulsion in the cup by the cup volume. Charges larger than 70 mm in diameter were initiated with a single 400 g Pentex PPP booster, whist smaller charges were initiated with a 150 g Pentex H booster. Velocity of detonation (VOD) was determined using an MREL Handitrap VOD recorder.

Procedure for Determining Distribution Function

Figure 12:
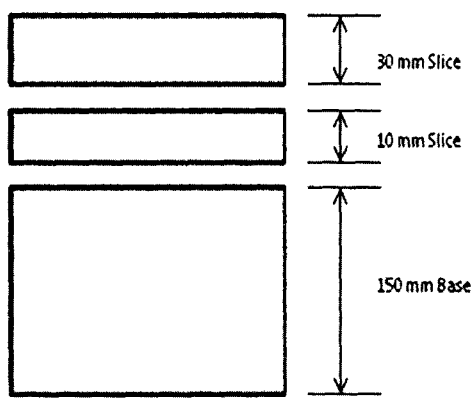
FIG. 12 is a schematic illustrating a container used for obtaining emulsion samples for determining distribution function.

Product samples were delivered from the pump rig described above into a 100 mm diameter cylindrical plastic container consisting of a 150 mm tall base, a 10 mm sample slice and a 30 mm tall top slice, as shown in FIG. 12. The three slices were joined together with masking tape to produce a cylinder which was filled to the top with emulsion. After filling, the upper 30 mm slice was removed and the emulsion scraped level on the top of the 10 mm slice with a flat stiff blade. A clear perspex plate was placed over the top of the 10 mm slice, and the entire container inverted. The 150 mm section was then removed, leaving the 10 mm section filled with emulsion sitting on the flat perspex plate. The emulsion was allowed to gas to completion prior to photography. The slice was illuminated from underneath using an x-ray viewer and photographed from above with a digital camera.

Figure 13:
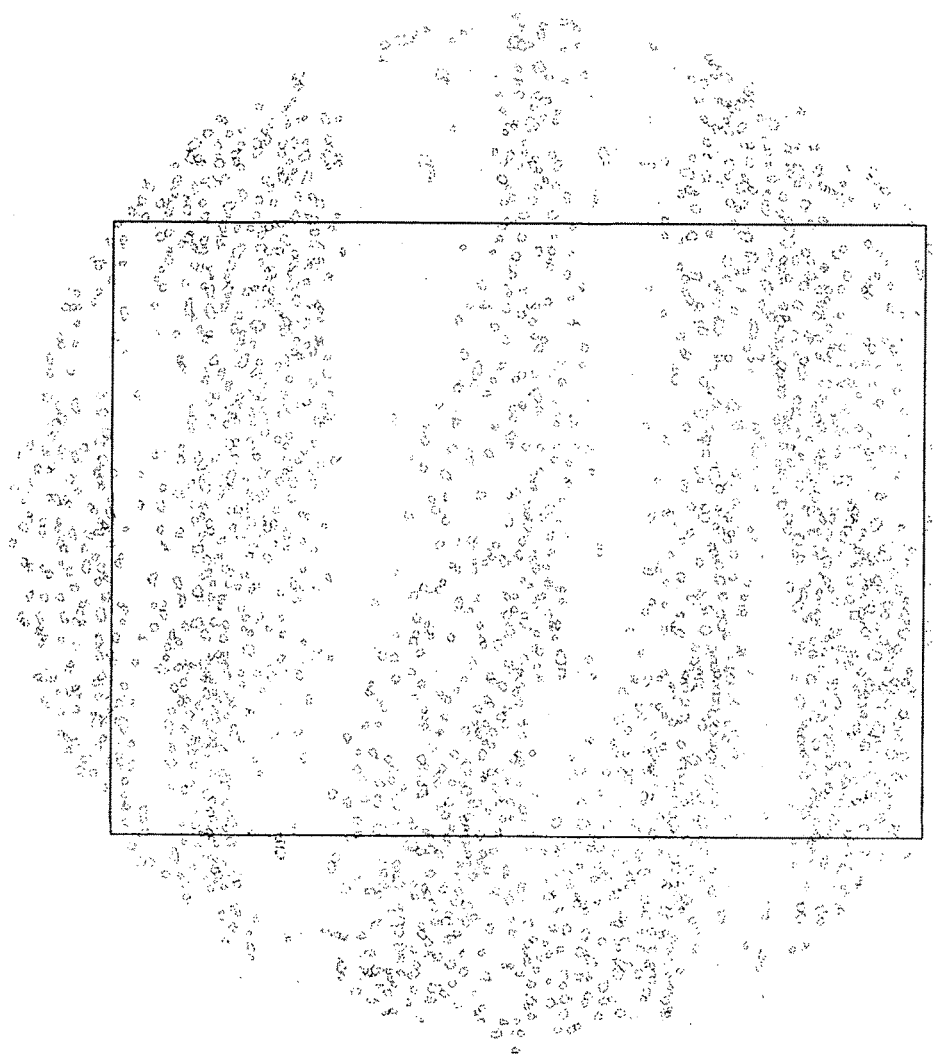
FIG. 13 is a processed image of an explosive material as referred to in the examples.

The photograph of the product structure was analysed using the Image) program. A rectangular section of the image was selected for distribution function analysis. FIG. 13 shows a typical image after processing and the rectangular section selected for DF analysis. The software enabled automatic detection of the bubbles in the photograph and produced a table showing the x and y position of the voids, the void perimeters and the void area. This data was exported to Mathcad for radial distribution function analysis.

The distribution function (DF) plots the fraction of emulsion that is within a given distance of a void surface. The DF procedure involved calculating the distance from each emulsion pixel to the nearest bubble surface. This program calculated the distance between a pixel and all of the bubble surfaces and returned the distance to the nearest bubble surface. The procedure was then repeated for all emulsion pixels. The frequency of emulsion points residing within a given distance to a bubble surface was then determined and plotted as a cumulative distribution. The differential of the cumulative fraction with respect to distance was also plotted against the cumulative fraction (also referred to as distribution function rate).

Example 1

Gassed Emulsion at 1.22 g/cm$^3$

This example demonstrates the performance of conventional gassed emulsion with random void distribution at a density of 1.22 g/cm$^3$.

The starting emulsion at a density of 1.32 g/cm$^3$ was delivered by a progressive cavity pump at a rate of 3 kg/min. A 4% mass sodium nitrite solution was injected into the flowing emulsion stream at a rate of 16 g/min by means of a gasser (gear) pump and dispersed in a series of static mixers. 1 m long cardboard tubes with internal diameters ranging from 40 to 180 mm were loaded with emulsion and allowed to gas. Charges were fired once the sample cup reached the target density of 1.22 g/cm$^3$.

Figure 16:
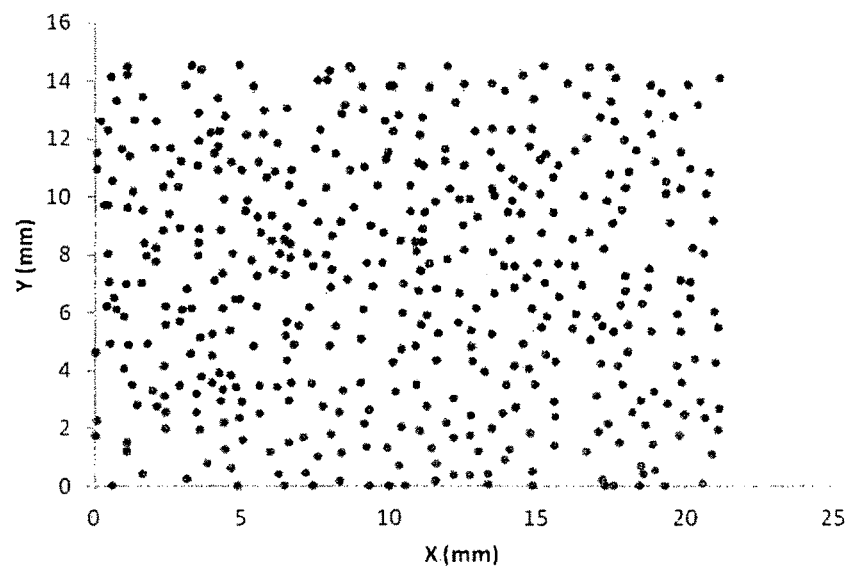
Figure 17:
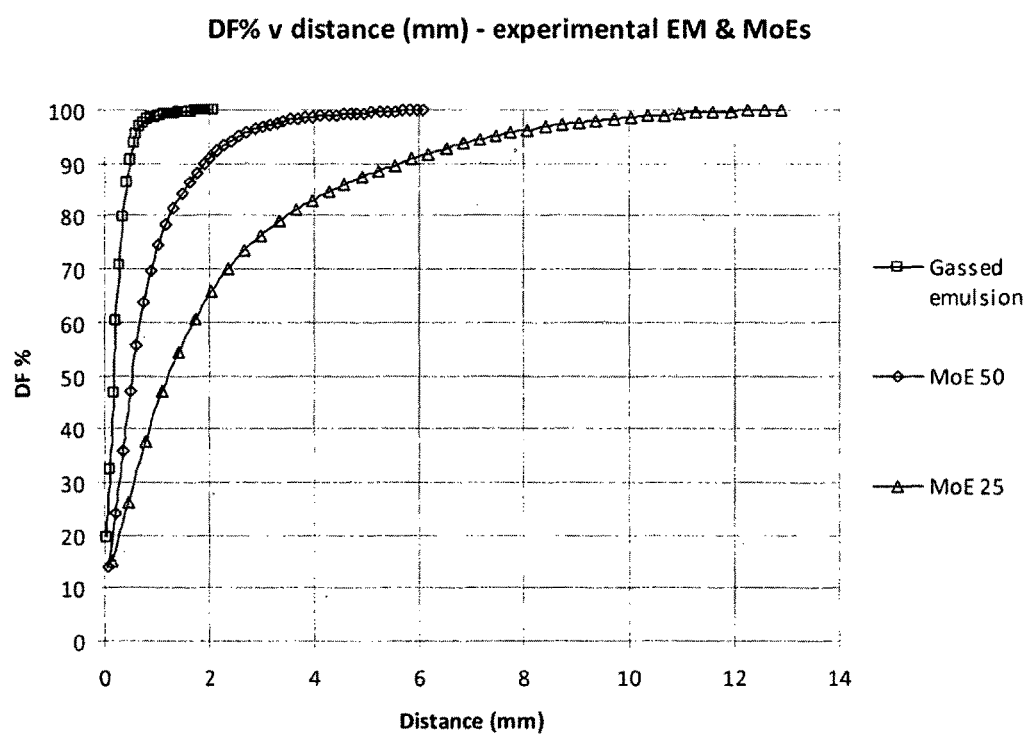
FIG. 17 is a plot of cumulative fraction versus separation distance for formulations referred to in the examples.
Figure 18:
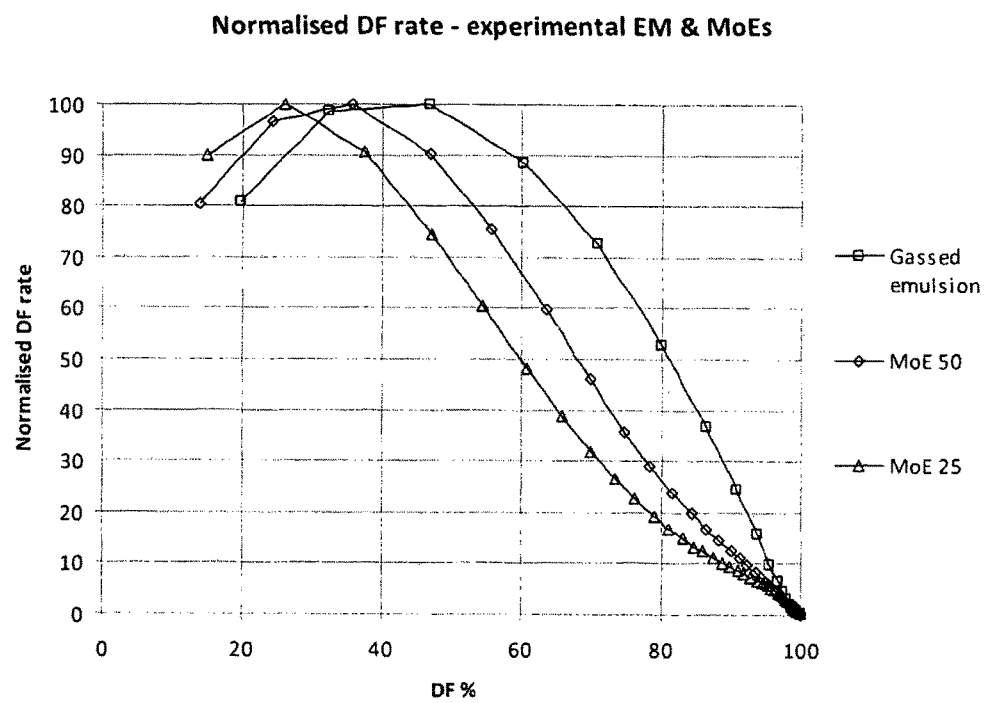
FIG. 18 is a plot of normalized distribution function rate versus cumulative fraction for formulations referred to in the examples.

A sample of the emulsion was taken for DF analysis according to the procedure described above. FIG. 16 shows the void positions for conventional gassed emulsion. The cumulative distribution function is plotted in FIG. 17 and the differential plotted in FIG. 18. The cumulative distribution function shows a steep curve, with the cumulative fraction rising to unity within a distance of approximately 0.7 mm. This indicates that 100% of the emulsion in the sample lies within 0.7 mm of a void surface. The differential of the distribution function (FIG. 18) shows a characteristic convex shape.

Figure 9:
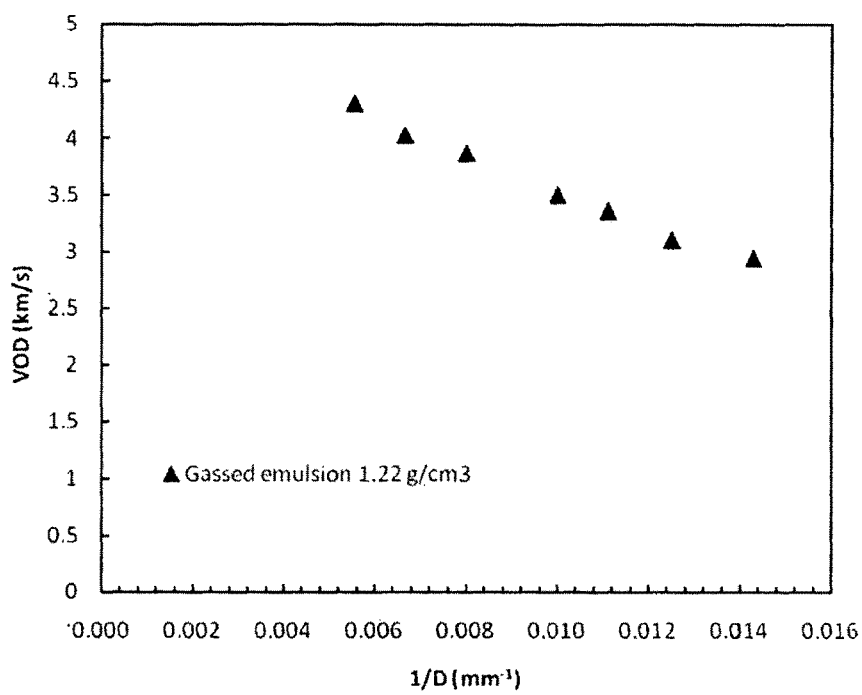
FIGS. 9-11 are graphs illustrating results obtained in the examples.

The VOD ranged from 2.9 km/s for the 70 mm diameter charge to 4.3 km/s at 180 mm. Charges smaller than 70 mm failed to sustain detonation. The VOD results are illustrated in FIG. 9.

Example 2

MOE25 at 1.22 g/cm$^3$

This example demonstrates the performance of MOE25, i.e. a mixture of emulsion with 25% mass sensitized and 75% unsensitized emulsion and was prepared using the apparatus described above.

The base emulsion (density 1.32 g/cm$^3$) was delivered by two progressive cavity pumps, PC1 and PC2. The base emulsion formulation was identical to Example 1 and was the same for both pumps. PC1 pumped ungassed emulsion at a flow rate of 4 kg/min. PC2 delivered emulsion at 1.3 kg/min with gasser (4% NaNO$_2$ solution) injected by a gasser (gear) pump. The emulsion was blended by a static mixer consisting of three helical mixing elements and loaded into cardboard tubes with internal diameters ranging from 70 to 180 mm. The gassed emulsion target density was 0.99 g/cm$^3$ providing an overall density of 1.22 g/cm$^3$ for the mixture of gassed and ungassed emulsion.

Figure 15:
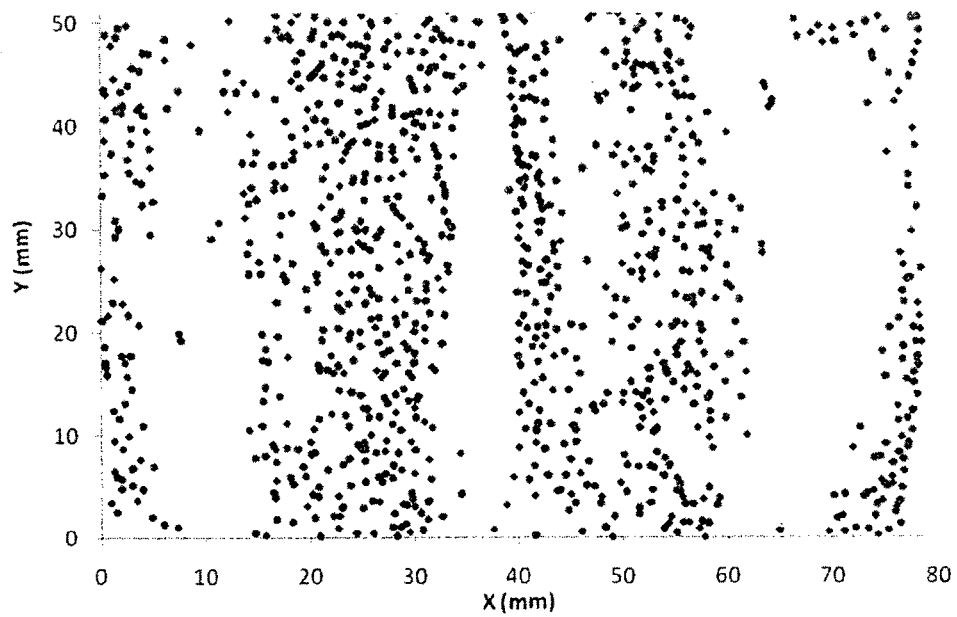

A sample of the emulsion was taken for DF analysis according to the procedure described above. The void positions in this sample are shown in FIG. 15. The cumulative distribution function is plotted in FIG. 17 and the differential plotted in FIG. 18. Compared to the gassed emulsion curve, the cumulative distribution for MOE25 exhibits a significantly shallower slope, with a long tail that extends out to a distance of approximately 6 mm. The plot of the distribution function differential can also be distinguished from the gassed emulsion sample by the presence of a point of inflexion in the curve and a concave tail section.

Figure 10:
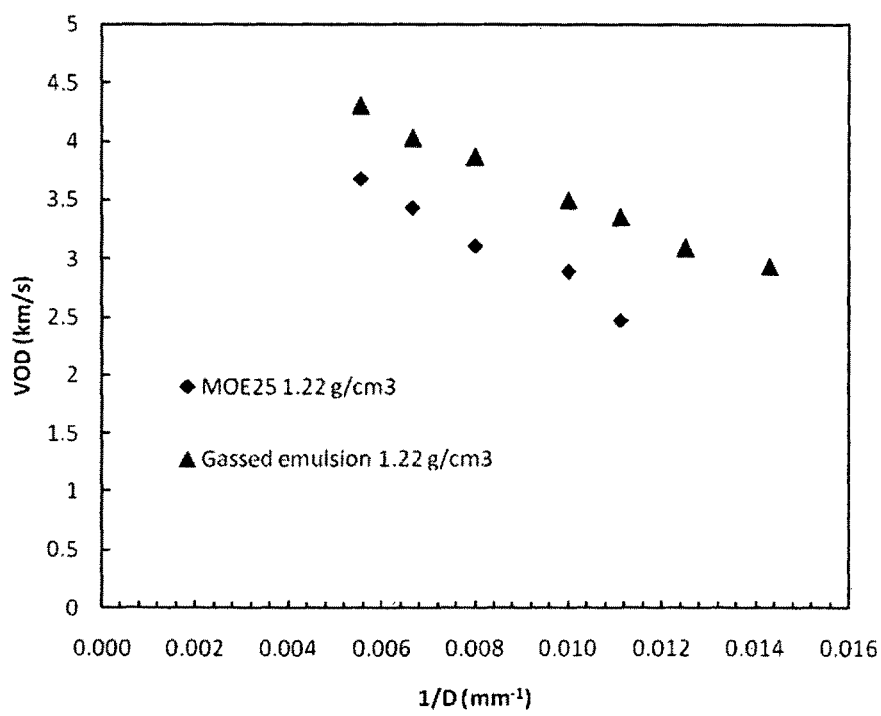

These changes in the distribution function and differential distribution function are reflected in the VOD measurements, shown in FIG. 10. The VOD ranged from 2.5 km/s for the 90 mm charge to 3.7 km/s at 180 mm, a significant reduction relative to conventional gassed emulsion described in Example 1. Charges with diameters smaller than 90 mm failed to sustain detonation. The reduced VOD in this example demonstrates the effect of the distribution function and differential distribution function on the shock/heave energy ratio. The shallower slope of this distribution function, the point of inflexion and the concave portion of the differential distribution function result in increased heave energy relative to conventional gassed emulsion, which exhibits a steeply sloped distribution function and convex differential distribution function.

Example 3

MOE50 at 1.22 g/cm$^3$

This example demonstrates the performance of MOE50, i.e. a mixture of emulsion with 50% mass gassed and 50% ungassed emulsion.

MOE50 was prepared using the apparatus mentioned in Example 2. The base emulsion (density 1.32 g/cm$^3$) was delivered by two progressive cavity pumps, PC1 and PC2 and was identical to the previous two examples. PC1 pumped ungassed emulsion at a flow rate of 3 kg/min. PC2 delivered emulsion at 3 kg/min with gasser (4% NaNO$_2$ solution) injected by a gasser (gear) pump. The emulsion was blended by a static mixer consisting of three helical mixing elements and loaded into cardboard tubes with internal diameters ranging from 70 to 180 mm. The gassed emulsion target density was 1.13 g/cm$^3$ providing an overall density of 1.22 g/cm$^3$ for the mixture of gassed and ungassed emulsion.

Figure 14:
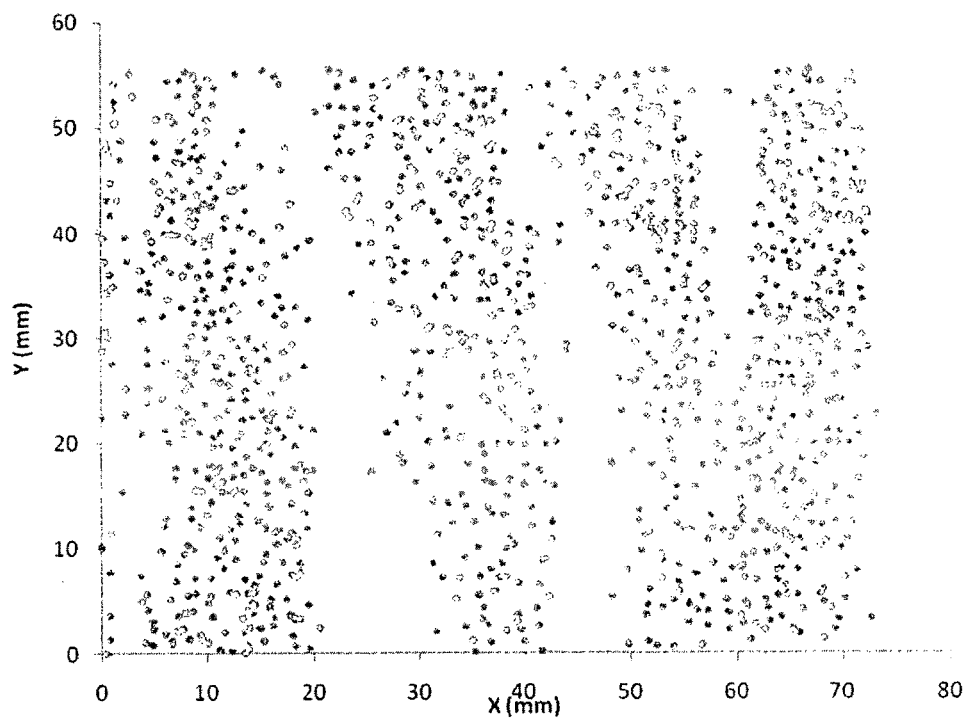
FIGS. 14-16 are plots of bubble position against distance as referred to in the examples.

A sample of the emulsion was taken for DF analysis according to the procedure described above. The void positions in this sample are shown in FIG. 14. The cumulative distribution function is plotted in FIG. 17 and the differential plotted in FIG. 18. The MOE50 sample exhibits a distribution function curve with an intermediate slope between conventional gassed emulsion and the MOE25 described in Examples 1 and 2, respectively. Likewise, the differential distribution function lies between the conventional gassed emulsion and MOE25, exhibiting a point of inflexion and a slight concave section.

Figure 11:
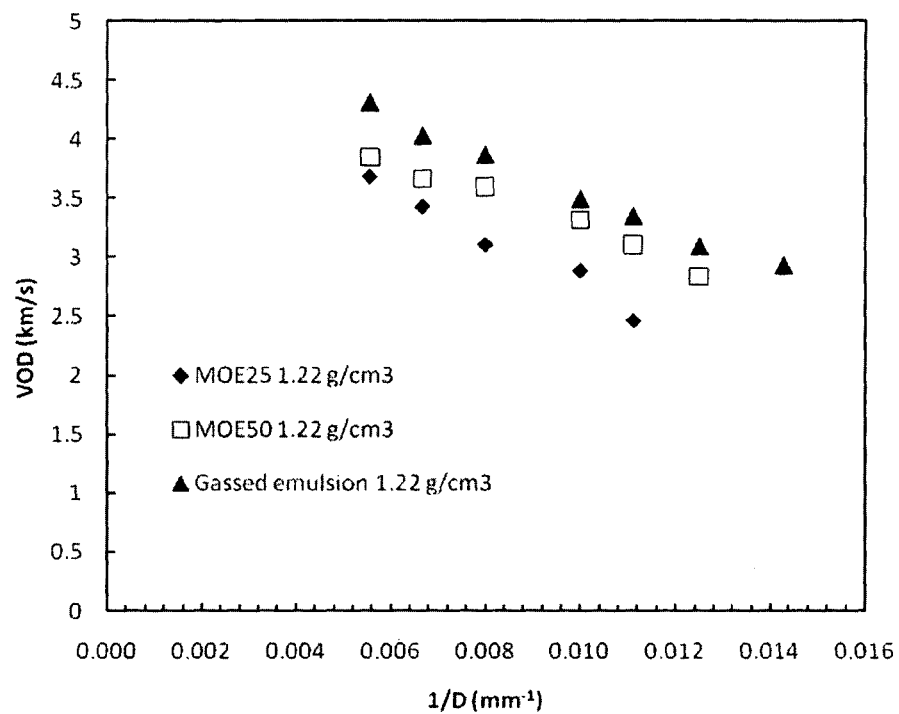

The VOD ranged from 2.8 km/s for the 80 mm charge to 3.9 km/s at 180 mm and is illustrated in FIG. 11. Charges with diameters smaller than 80 mm failed to sustain detonation. VOD results for MOE50 were between those of gassed emulsion and MOE25. This demonstrates that this explosive, with intermediate distribution and differential distribution functions relative to Examples 1 and 2, exhibits an intermediate shock/heave energy ratio. Importantly, the example demonstrates that the present invention allows tailoring of explosive performance (i.e. shock/heave energy balance) to suit different blasting applications by suitable selection of a distribution function template at the same overall explosive density. That is, the invention allows manipulation of the shock/heave energy balance whilst maintaining the same total energy of the explosive.

Figure 19:
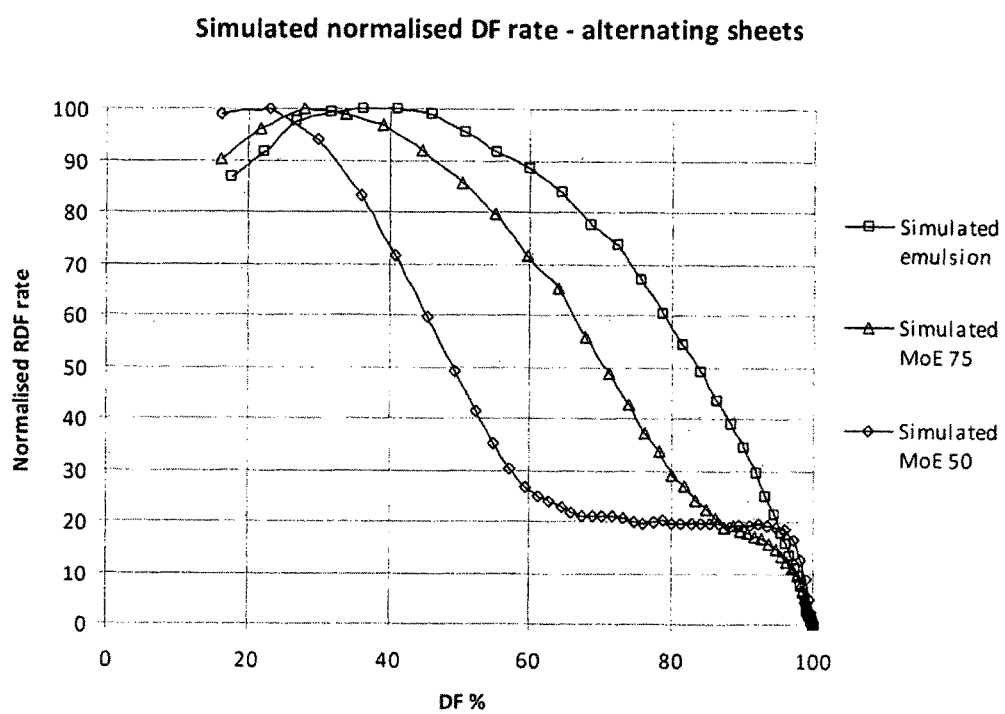
FIG. 19 is a plot of distribution function rate versus cumulative fraction for simulated formulations referred to in the examples

The DF of an emulsion with a perfectly random distribution of voids, and that of two idealized (simulated) MoEs with the sensitized and unsensitized regions arranged as alternating flat sheets in which no voids have strayed into the unsensitized region, is shown in FIG. 19. The simulated emulsion DF is almost identical to the experimental emulsion. The idealised MoEs however have sharper corner turning in the graphs than the experimental MoEs. The replacement of the sharper corners of the idealized MoE with the smoother concave graphs of the experimental emulsion results from a slightly more diffuse distribution of the voids into the unsensitized regions in the experimental emulsion compared to the simulated MoEs.

Noting the results obtained in the examples, the present invention also provides explosive compositions comprising sensitizing voids distributed in a liquid energetic materials that are believed to be new per se and that exhibit a characteristic distribution function that is different from known void-sensitized explosive formulations, such as emulsions, watergels and slurry formulations. More specifically, for the explosive compositions of the inventions a plot of distribution function rate versus distribution function includes a point of inflexion, and possibly a concave portion. In contrast corresponding plots for conventional explosive formulations exhibit a characteristic domed profile. As explained above, in this context the "distribution function" (or "distance froth void" function) is defined as "the fraction of the liquid that is within a given distance from any void surface", and the "distribution function rate" is defined as the differential of the "distribution function" with respect to the distance from any void surface.

In an embodiment, for the explosive compositions a plot of distribution function rate versus distribution function comprises a region extending from a distribution function value of 0% to between 10% and 90%, and wherein after the dome region the "distribution function rate" is between 1% and 50% of the peak of the dome. Preferably, the dome region extends from a "distribution function" value of 0% to between 15% and 85%, and in the region after the dome the "distribution function rate" is between 1.5% and 35% of the peak of the dome, Even more preferably the dome region extends from a "distribution function" value of 0% to between 20% and 80%, and in the region after the dome the "distribution function rate" is between 2% and 20% of the peak of the dome.

The invention claimed is:

1. A method of achieving a designed bulk detonation energy output in terms of a ratio of shock energy to heave energy for an explosives composition that comprises sensitizing voids distributed within liquid energetic material and that is formulated by blending together a void sensitized liquid energetic material and a void-free liquid energetic material, the method comprising:
    identifying a distribution function template that is representative of a desired ratio of shock energy to heave energy, the distribution function template being characterized by a blending ratio of void sensitized liquid energetic material to void-free liquid energetic material and by a characteristic dimension of void-free liquid energetic material relative to a mean diameter of voids in the void sensitized liquid energetic material;
    selecting a density for the explosive composition;
    providing a void sensitized liquid energetic material having a mean void diameter and a void-free liquid energetic material that, based on their respective densities and on the blending ratio, would achieve the density selected for the explosive composition; and
    formulating the explosive composition by blending together at the blending ratio the void sensitized liquid energetic material and the void-free liquid energetic material, wherein blending is carried out to achieve the characteristic dimension of void-free liquid energetic material relative to the mean diameter of voids in the void sensitized liquid energetic material consistent with the distribution function.

2. The method of claim 1, wherein the distribution function is non-Gaussian.

3. The method of claim 1, wherein the sensitizing voids are gas bubbles.

4. The method of claim 1, wherein the sensitizing voids are at least one of microballoons, or polystyrene.

5. The method of claim 1, wherein the liquid energetic material is an emulsion.

6. The method of claim 1, wherein the sensitizing voids are gas bubbles having a mean diameter between 20 and 2000 microns.

7. The method of claim 1, wherein the sensitizing voids have a density below 0.25 g/cc and wherein the voids have a mean diameter in the range of 20 to 2000 microns.

8. The method of claim 1, wherein the sensitizing voids are at least one of gas bubbles, glass microballoons, plastic microballoons, or expanded polystyrene beads having with a density below 0.25 g/cc and wherein the voids have a mean diameter in the range of 20 to 2000 microns.

9. The method of claim 8, wherein the mean diameter of voids is in the range 40 to 500 microns.

10. The method of claim 1, wherein the void-sensitized liquid energetic material and void-free liquid energetic material are blended by laminar mixing using a static mixer.

* * * * *